(12) United States Patent
Mermet et al.

(10) Patent No.: US 8,276,348 B2
(45) Date of Patent: Oct. 2, 2012

(54) STERILE PACKING AND STERILIZATION METHOD USING THIS PACKING

(75) Inventors: Emeric Mermet, Grenoble (FR); Thomas Dubois, Grenoble (FR)

(73) Assignee: Becton Dickinson France, S.A.S. (FR)

( * ) Notice: Subject to any disclaimer, the term of this patent is extended or adjusted under 35 U.S.C. 154(b) by 111 days.

(21) Appl. No.: 12/600,143

(22) PCT Filed: Jun. 9, 2008

(86) PCT No.: PCT/IB2008/002684
§ 371 (c)(1),
(2), (4) Date: Nov. 13, 2009

(87) PCT Pub. No.: WO2009/150488
PCT Pub. Date: Dec. 17, 2009

(65) Prior Publication Data
US 2012/0117920 A1    May 17, 2012

(51) Int. Cl.
*B65B 55/04* (2006.01)
(52) U.S. Cl. ......... 53/425; 53/426; 53/432; 53/449; 53/510; 53/171; 53/173; 422/292; 422/295
(58) Field of Classification Search ......... 53/425, 53/426, 111 R, 432, 405, 408, 449, 510, 170, 53/173; 422/292, 300, 26, 28, 33, 295; 206/438
See application file for complete search history.

(56) References Cited

U.S. PATENT DOCUMENTS

| | | | | |
|---|---|---|---|---|
| 4,155,494 A * | 5/1979 | Poncy et al. | ........... | 223/111 |
| 4,569,377 A * | 2/1986 | Ellis | ........... | 141/98 |
| 5,391,350 A * | 2/1995 | Wagner | ........... | 422/26 |
| 5,447,699 A * | 9/1995 | Papciak et al. | ........... | 422/294 |
| 5,580,530 A * | 12/1996 | Kowatsch et al. | ........... | 422/559 |
| 5,735,609 A * | 4/1998 | Norton | ........... | 383/33 |
| 5,870,886 A * | 2/1999 | Norton | ........... | 53/492 |
| 6,406,674 B1 | 6/2002 | Bourne et al. | | |
| 7,273,594 B2 * | 9/2007 | Lin et al. | ........... | 422/292 |
| 7,318,548 B2 * | 1/2008 | Felice et al. | ........... | 232/45 |
| 7,827,770 B2 * | 11/2010 | Rocholl et al. | ........... | 53/469 |
| 2006/0042192 A1 * | 3/2006 | Levy et al. | ........... | 53/432 |
| 2011/0123396 A1 * | 5/2011 | Mermet et al. | ........... | 422/33 |

FOREIGN PATENT DOCUMENTS
DE    3717916 A1    12/1988
* cited by examiner

*Primary Examiner* — Hemant M. Desai
*Assistant Examiner* — Gloria R Weeks
(74) *Attorney, Agent, or Firm* — Hoffmann & Baron, LLP

(57) ABSTRACT

The packing according to the invention comprises: a container for holding said at least one object to be sterilized, having an inlet opening and a discharge opening via which said at least one object may pass into and out of said container, said container comprising a rigid part which comprises a peripheral wall bored with a multitude of small holes having dimensions smaller than those of the said at least one object, and a non-rigid part in a material porous to the sterilization fluid and non-porous to microbial contamination, this non-rigid part being able to contain said rigid part and to be sealed thereon; and at least one envelope made in a flexible and airtight material, which is vacuum sealing fitted on said container.

13 Claims, 3 Drawing Sheets

STERILE PACKING AND STERILIZATION METHOD USING THIS PACKING

BACKGROUND OF THE INVENTION

The present invention concerns a sterile packing and a sterilization method using this packing.

Some activities involve transporting sterile parts or components in sterile packing. This is the case in particular for the component parts of syringes, which must be transported between the production site and an assembly site, to form the syringe, and fill the syringe bodies.

A known sterilization method used for syringe parts consists of placing these parts in packings made of a flexible and airtight material, then exposing these packings thus filled to gamma rays. This method has the drawback, for the syringe manufacturer, of having to pack the non-sterilized parts in non-sterile packings, then to transmit these packings to a service provider specialized in this type of sterilization, which, after sterilization, transmits these packings to the purchaser of the parts, for assembly and/or filling of the syringes. The use of a specialized sub-contractor of this type constitutes a notable constraint for the syringe manufacturer.

Another known sterilization method in such an application uses water vapor to sterilize the parts and their packing. This sterilization method is preferred to the radiation sterilization method because it is well-received by the pharmaceutical industry using the syringes, or even required by some users, or is also made obligatory by the nature or material of the packed parts or components. There are not, however, packings making it possible to ensure the perfect performance of sterilization during the sterilization method and, after transport, the perfect preservation of the integrity of the packing all the way to the end user.

BRIEF SUMMARY OF THE INVENTION

The present invention aims to resolve the abovementioned drawbacks.

Its aim is therefore to provide a packing making it possible to ensure the perfect performance of a sterilization of one or several objects to be sterilized, in particular through water vapor, to ensure perfect preservation of sterility during transport and storage of the packing, and to immediately detect any loss of integrity of the packing, and therefore any loss of sterility thereof. The invention also aims to provide a sterilization method using this packing, making it possible to sterilize said objects whiles ensuring the perfect performance of the sterilization thereof.

The term "object" will be used below generically to generally designate one or several parts or components to be packed; this term must be understood in the broadest sense, covering all types of part(s), product(s) or component(s), and in particular all component parts of syringes.

To achieve the abovementioned objectives, the packing according to the invention comprises:

a container for holding said at least one object to be sterilized, having an inlet opening and a discharge opening via which said at least one object may pass into and out of said container, said container comprising a rigid part which comprises a peripheral wall bored with a multitude of small holes having dimensions smaller than those of the said at least one object, and a non-rigid part in a material porous to the sterilization fluid and non-porous to microbial contamination, this non-rigid part being able to contain said rigid part and to be sealed thereon; and at least one envelope made in a flexible and airtight material, which is vacuum sealing fitted on said container.

The sterilization and packing method according to the invention comprises the steps consisting of:

in any order:
  filling said rigid part of the abovementioned container with at least one object to be sterilized;
  closing said inlet opening and said discharge opening using said non-rigid part;
sterilizing the container using said sterilization fluid;
placing the container, thus sterilized, in said at least one envelope;
creating a vacuum inside said at least one envelope, and
sealing this at least one envelope around the container while the vacuum inside said at least one envelope is maintained.

The invention thus consists of using a container comprising a rigid part bored with a multitude of holes through its wall, to receive the object(s) to be sterilized. The rigidity of this rigid part makes it possible to preserve the integrity of this or these object(s) during the later vacuum operation, which is necessary when this or these object(s) are liable to deform or deteriorate under the exertion of prolonged mechanical stresses exerted on them, as is the case for example for syringe plungers. This rigidity also has the advantage of granting a fixed shape to a set of objects, optimized for a homogenous exposure to a sterilization fluid, in particular water vapor, which is a crucial parameter for the performance of such a sterilization. In other words, said rigid part makes it possible to eliminate any piles of objects which would be made possible with a flexible container, causing a risk of the fluid not sufficiently penetrating to the heart of this pile to ensure the required sterilization. The rigidity of said rigid part also has the advantages of making it possible to increase the capacity of a packing relative to the maximum capacity which a known flexible packing can have, and to facilitate the treatments and manipulations done by operators.

The multiple openings of this rigid part of the container and the porosity of said non-rigid part allow a sufficient diffusion of the sterilization fluid inside said non-rigid part, said rigid part and around all of the objects contained in this rigid part; the closing of the non-rigid part by sealing makes it possible to preserve the integrity of the sterilization done to the objects, said rigid part and the internal surface of the non-rigid part.

Placing the packing under vacuum using said envelope makes it possible to perfectly protect the object(s) with regard to the environment, and the application of this envelope around the container constitutes an indication of the absence of penetration of air inside this container, and therefore indicates the preservation of the sterility of the packing.

The packing and the method according to the invention thus have the determining advantages of allowing effective sterilization of objects by a sterilization fluid, in particular by water vapor, perfectly preserving the integrity of these packed objects, and making it possible to immediately indicate any loss of integrity, and therefore sterility, of the packing.

The material of said at least one first membrane comprises pores whereof the size can go from 2 to 15 microns and a Log Reduction Value (as defined in the ASTM F-1608 standard) greater than or equal to 3. This can be a film marketed by the company Du Pont De Nemours under the TYVEK® brand, references 1073B, 2FS or 1059B, or the complex marketed by the company WIPAK under the WIPAK® brand, references Paper 80B or Paper 120B.

Preferably, the container includes a connection ring on its discharge opening, or close to this discharge opening, able to be connected to a sterile enclosure wherein said at least one object is intended to be transferred, and being located inside said at least one envelope.

The connection of the container to said sterile enclosure for the transfer of objects into this enclosure can, thanks to this ring, be done under the best conditions, the transfer being perfectly aseptic and ensuring the maintenance of sterility during its progress.

Said connection ring can in particular be of the type described in documents U.S. Pat. No. 6,571,540 and U.S. Pat. No. 6,817,143.

Said non-rigid part can be separated from this connection ring, or can be sealably connected to this connection ring.

Said rigid part of the container can be connectable at least to one part of said connection ring, to allow a facilitated discharge of the object(s).

In this case, advantageously, the part of the connection ring which is not connected to said rigid part of said container is contained in a sterile envelope. This sterile envelope is open so as to uncover the connection ring in order to allow the connection of this ring to the sterile enclosure.

Said rigid part of said container can be able to be separated from said connection ring.

Said rigid part of the container can be able to be connected to said connection ring via connection means. In this case, advantageously, said connection means are such that they maintain said rigid part of the container in a position coaxial to said connection ring.

This coaxial maintenance facilitates the discharge of objects into said sterile enclosure when said connection ring is connected to this enclosure.

The wall of the container defining said discharge opening can be formed to engage with said connection ring.

Said connection ring can also comprise a removable door, intended to be removed after connection of said ring to the sterile enclosure.

The sterile packing can also comprise a lid able to be connected to said rigid part of the container.

In the packing according to the invention, said non-rigid part can be formed of a plurality of layers.

This plurality of layers minimizes the risk of a loss of integrity of the packing if a hole appears in one layer. Moreover, the risk of having aligned holes decreases as the number of layers increases.

The invention will be well understood, and other characteristics and advantages thereof will appear, in reference to the appended diagrammatic drawing, showing, as a non-limiting example, one preferred embodiment of the sterile packing it concerns.

BRIEF DESCRIPTION OF THE SEVERAL VIEWS OF THE DRAWING(S)

DETAILED DESCRIPTION OF THE INVENTION

Figure 7:
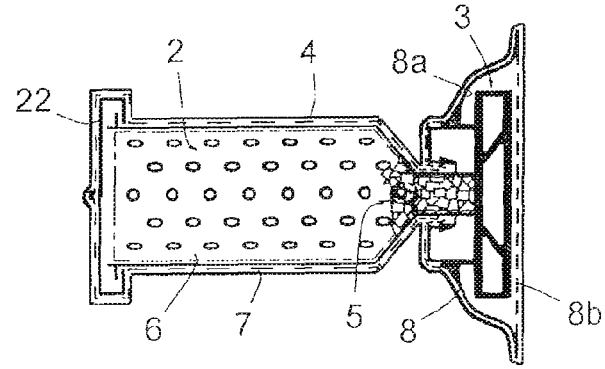
FIG. 7 is a similar view of the sterile packing, as it is obtained after vacuum sealing of said envelope on said sub-assembly.

FIG. 7 shows a sterile packing 1 formed by a container 2 including a connection ring 3 and an exterior envelope 4.

The container 2 is intended to contain one or several objects 5 to be sterilized, in particular component parts of syringes, and in particular syringe plungers. As shown more particularly by FIGS. 1 to 4, it comprises an internal part formed by a container 6 and an external part formed by envelopes 7 and 8.

Figure 1:
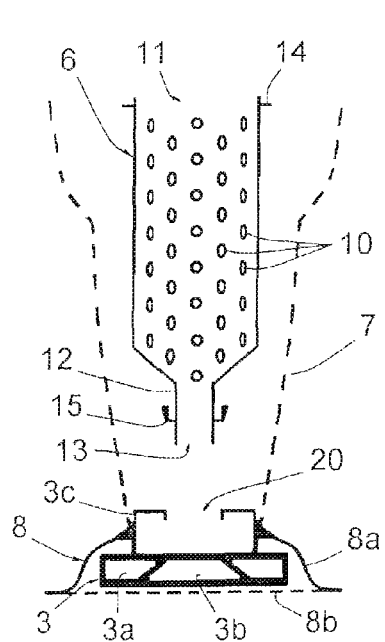
FIGS. 1 to 4 are very simplified cross-sectional views of different component pieces of this packing, during different successive phases of assembling these pieces.

The container 6 is rigid. It comprises a peripheral wall bored with a multitude of small holes 10 having dimensions smaller than those of the objects 5. As shown by FIG. 1, this peripheral wall defines, at one end, an upper opening 11 for allowing the objects 5 in and forms, at the other end, a conduit 12 ending by a lower opening 13 for the discharge of the objects 5. The container 6 also comprises, set back from its upper edge, a flange 14 able to receiving a closing lid 22, and, set back from its lower opening 13, a flange 15 provided with a deformable peripheral skirt, forming a lock means.

The external envelope 7 is flexible. It has a tubular shape and is connected, at its lower part, to the connection ring 3; it is dimensioned to contain the container 6 and comprises an upper portion enabling it to be closed by sealing on the upper end of this container 6, as appears in FIG. 4.

This envelope 7 is made in a material porous to the sterilization fluid and not porous to microbial contamination. This material comprises pores whereof the size can go from 2 to 15 microns and a Log Reduction Value (as defined in the ASTM F-1608 standard) greater than or equal to 3. This can be a film marketed by the company Du Pont De Nemours under the TYVEK® brand, references 1073B, 2FS or 1059B, or a complex marketed by the company WIPAK under the WIPAK® brand, references Paper 80B or Paper 120B.

The envelope 8 is connected to the connection ring 3 and is dimensioned to completely envelop this ring 3. It comprises a non-porous peripheral wall 8a and an end wall 8b, sealed on the peripheral edge of the wall 8a, in a material porous to the sterilization fluid and not porous to microbial contamination. This material can in particular be the same as that constituting the envelope 7.

The connection ring 3 comprises a circular seat 3a and a removable door 3b. The circular seat 3a comprises means for the connection of the ring 3 to a sterile enclosure for manipulation of the objects 5, and defines a central discharge opening for these objects 5. The removable door 3b is, at this stage of use of the packing 1, maintained on the seat 3a such that it covers said discharge opening 13. This ring is of a known type, for example of the type described in documents U.S. Pat. No. 6,571,540 and U.S. Pat. No. 6,817,143, and therefore will not be described in more detail.

Figure 2:
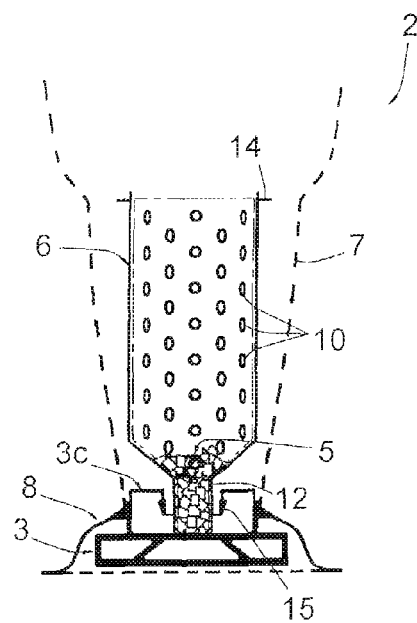
Figure 3:
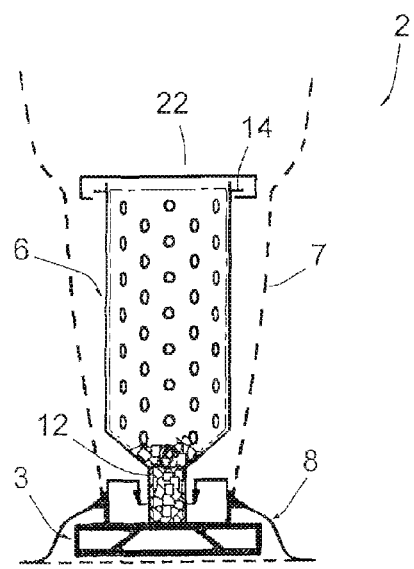

The connection ring 3 also comprises an extension 3c integral with the seat 3a, having a peripheral wall and a transverse wall. The peripheral wall comprises envelopes 7 and 8 sealed on it. The transverse wall defines an opening 20 coaxial to said central discharge opening defined by the seat 3a; as shown in FIG. 2, this opening 20 is intended to receive, through it, the discharge conduit 12, until it comes from the lower end of this conduit bearing against the door 3b, then the flange 15. The skirt comprised by the latter locks by snapping behind said transverse wall at the moment when said discharge conduit 12 bears against the door 3b. The container 6 is thus maintained in a position coaxial to the connection ring 3.

Once this connection of the container 6 and the ring 3 is done, the container 6 is filled with objects 5, as shown by FIG. 2. Out of a concern for clarity in the drawing, these objects 5 have been only partially illustrated, the overall contour they form being defined by a dashed line.

Figure 4:
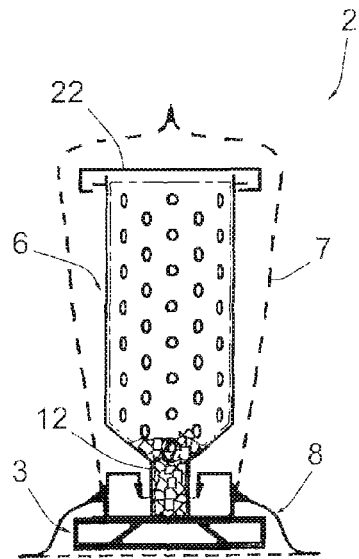

The container 6 then receives the aforementioned closing lid 22 (cf. FIG. 3), whereof the assembly to the flange 14 can be done in particular by clipping, then the envelope 7 is sealed above this lid 22, as shown in FIG. 4.

Figure 5:
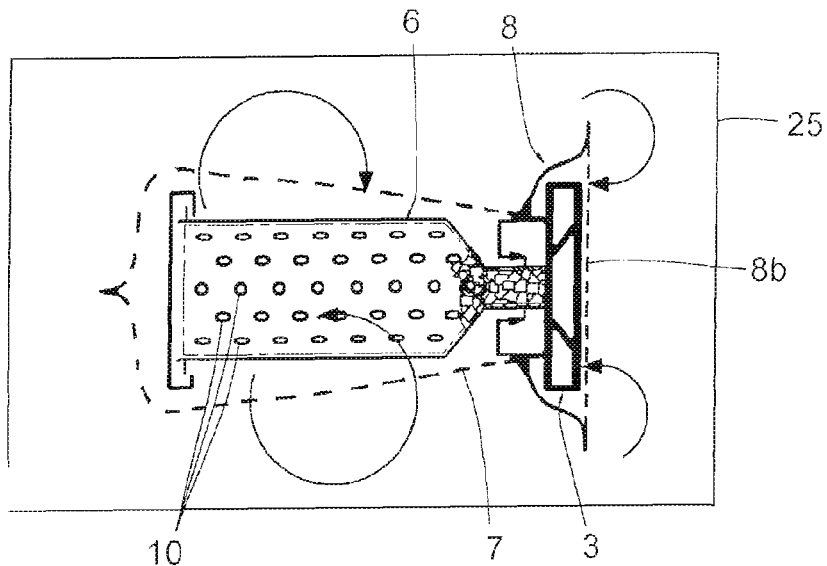
FIG. 5 is a view of the sub-assembly shown in FIG. 4, when it is placed in a sterilization enclosure.

The container 2 thus formed is placed in a sterilization enclosure 25, as appears in FIG. 5, wherein a sterilization fluid circulates, in particular water vapor. This fluid, shown by circular arrows, penetrates through the pores of the envelope 7, through multiple holes 10 of the wall of the container 6 and through the pores of the wall 8b of the envelope 8, which allows a sufficient diffusion of this sterilization fluid inside the envelopes 7 and 8, the container 6 and around the objects 5. Once the sterilization is done, the closing of the envelope 7 by sealing makes it possible to preserve the integrity of this sterilization for the objects 5, the container 6 and the internal surfaces of the envelopes 7 and 8.

Figure 6:
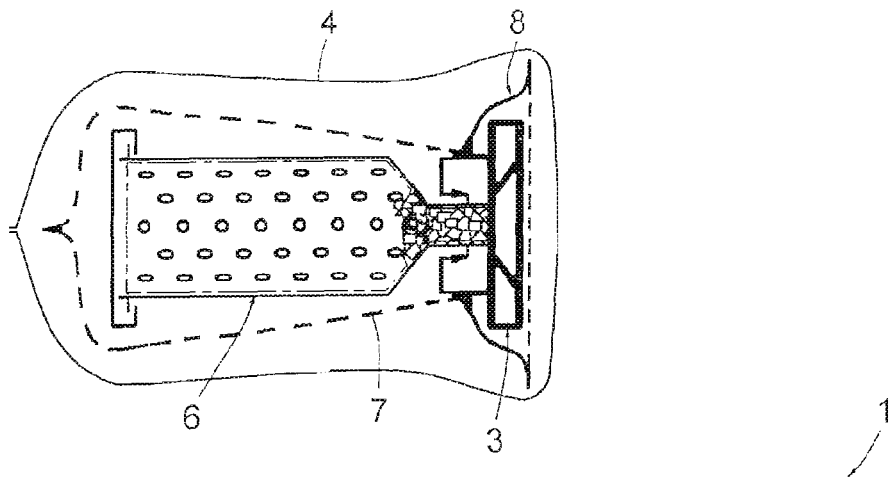
FIG. 6 is a similar view of this same sub-assembly, placed in an envelope.

The envelope 4, visible in FIG. 6 in the non-sealed state, is formed of a flexible and airtight material, in particular in a synthetic material. The sterilized container 2 is placed in this envelope 4, then a vacuum is created inside the envelope 4, and therefore also inside the envelope 7 and the container 6; the envelope 4 is then vacuum sealed on the container 2, as shown in FIG. 7, thereby making it possible to obtain the packing 1.

This evacuation of this packing 1 thanks to the envelope 4 makes it possible to perfectly protect the objects 5 with regard to the environment, and the application of this envelope 4 around the container 2 constitutes an indicator of the absence of penetration of air inside this container 2, and therefore an indicator of the preservation of the sterility of the packing 1.

The rigidity of the container 6 makes it possible to preserve the integrity of the objects 5 during the evacuation operation, which is necessary when these objects are liable to deform or deteriorate under the exertion of the prolonged mechanical stresses exerted on them, as is the case for example for syringe plungers. This rigidity also has the advantage of granting a fixed shape to the assembly formed by these objects, optimized for a homogenous exposure to the sterilization fluid, which is a crucial parameter for performance of the sterilization. In other words, the container 6 makes it possible to eliminate all piles of objects which would be made possible with a flexible container, causing a risk of the fluid not sufficiently penetrating to the heart of this pile to ensure the required sterilization. The rigidity of the container 6 also has the advantages of making it possible to increase the capacity of a packing relative to the maximum capacity which a known flexible packing can have, and facilitating the treatments and manipulations done by operators.

Figure 8:
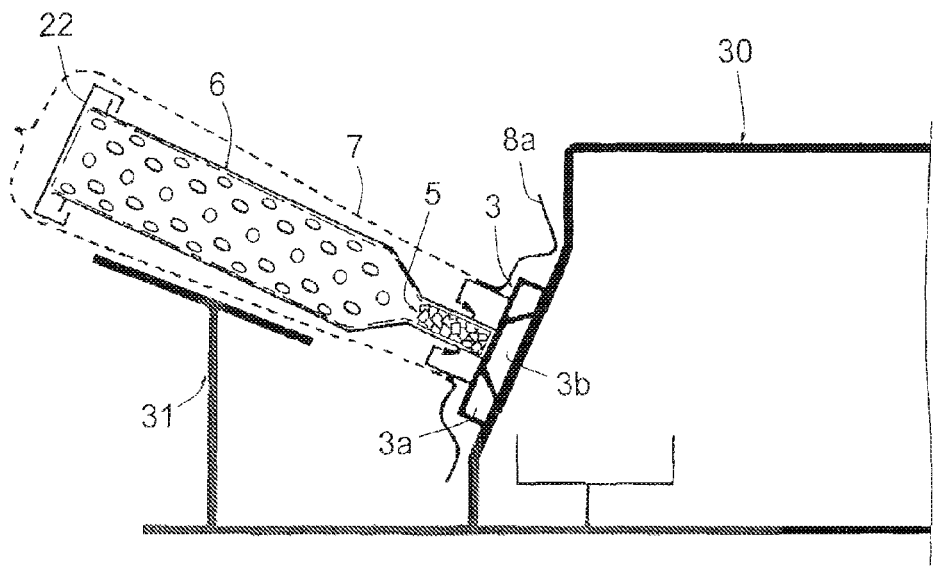
FIG. 8 is a view of the packing after removal of said envelope and connection to a sterile enclosure, before opening of a removable door it comprises.
Figure 9:
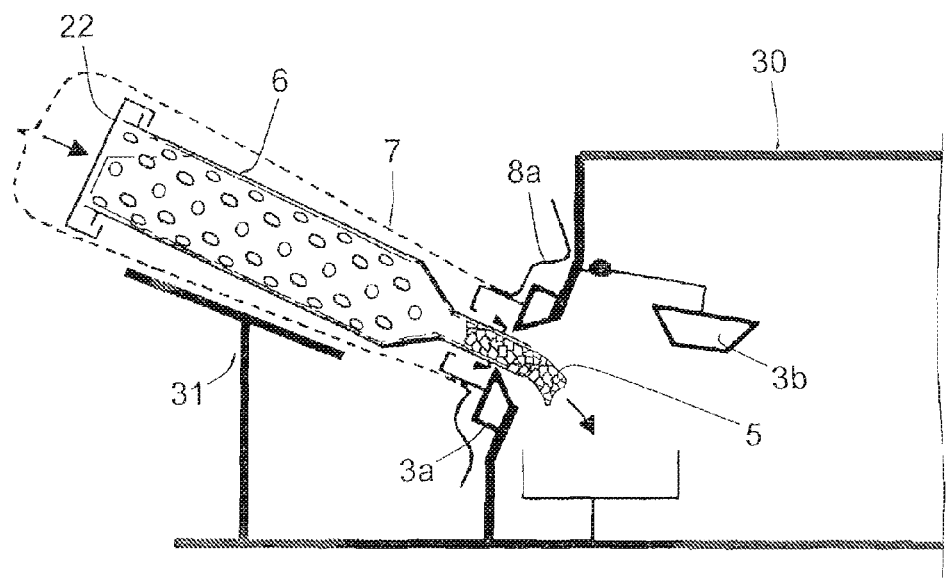
FIG. 9 is a view of the packing similar to FIG. 8, after opening of said door.

The transfer of the objects 5 into a sterile enclosure 30 as shown in FIGS. 8 and 9 is done by opening and removing the envelope 4, then opening the envelope 8, connecting the seat 3a of the ring 3 to the corresponding seat arranged on the enclosure 30 (cf. FIG. 8), then opening the door 3b (cf. FIG. 9). The connection of the seat 3a to the seat of the enclosure 30 is facilitated by the bearing of the packing 1 on a support 31 placed in the appropriate place.

In reference to FIG. 9, it appears that the mobility of the rigid container 6 in the flexible envelope 7 makes it possible to engage the discharge conduit 12 through the central discharge opening defined by the seat 3a, and therefore to preserve the objects 5 from all contact with a potentially contaminated surface of this seat 3a or of said corresponding seat of the enclosure 30. As appears from the preceding, the invention provides a sterile packing and a sterilization method using this packing, having the determining advantages of allowing an effective sterilization of the objects by a sterilization fluid, in particular water vapor, of perfectly preserving the integrity of the packed objects, and enabling an immediate indication of any loss of integrity, and therefore sterility, of the packing.

It must be specified that the embodiment of the invention described above was provided purely as an example. It goes without saying that the invention is not limited to this embodiment, but that it extends to all embodiments covered by the appended claims.

The invention claimed is:

1. Sterile packing for containing at least one object (5) to be sterilized by a sterilizing fluid, characterized in that the sterile packing comprising:
   a container (2) for holding the at least one object (5) to be sterilized and having an inlet opening (11) and a discharge opening (13) via which said at least one object (5) may pass into and out of said container (2), said container (2) comprising a rigid part (6) having a bored peripheral wall with a multitude of small holes (10) having dimensions lower than those of the said at least one object (5), and a non-rigid part (7) in a material porous to the sterilizing fluid and non-porous to microbial contamination, said non-rigid part (7) being able to contain said rigid part (6) and to be sealed thereon; and
   at least one envelope (4) made in a flexible and airtight material, which is vacuum sealing fitted on said container (2).

2. Sterile packing according to claim 1, characterized in that the container (2) includes a connection ring (3) at or proximate to said outlet opening (13) of said container (2) and being connectable to a sterile enclosure (30) in which the at least one object (5) is intended to be transferred, said connection ring being provided inside said at least one envelope (4).

3. Sterile packing according to claim 2, characterized in that said non-rigid part (7) of said container (2) is separated from the connection ring (3).

4. Sterile packing according to claim 2, characterized in that said rigid part (6) of said container (2) is connectable to at least a part (3c) of said connection ring (3).

5. Sterile packing according to claim 4, characterized in that the part (3a, 3b) of the connection ring (3) that is not connected to said rigid part (6) of said container (2) is contained in a sterile envelope (8).

6. Sterile packing according to claim 2, characterized in that said rigid part (6) of said container (2) is separable from said connection ring (3).

7. Sterile packing according to claim 2, characterized in that said rigid part (6) of said container (2) is connectable to said connection ring (3) by connection means (15, 20).

8. Sterile packing according to claim 7, characterized in that said connection means (15, 20) are such that they maintain said rigid part (6) of said container (2) in a coaxial position with respect to said connection ring (3).

9. Sterile packing according to claim 2, characterized in that the wall (12) of the container (2) delineating said discharge opening (13) is engageable with said connection ring (3).

10. Sterile packing according to claim 9, characterized in that said connection ring (3) further comprises a removable door (3b), intended to be withdrawn after connection of said connection ring (3) to said sterile enclosure (30).

11. Sterile packing according to claim 1, characterized in that it further comprises a lid (22) connectable with said rigid part (6) of said container (2).

12. Sterile packing according to claim 1, characterized in that said non-rigid part (7) of said container (2) is made of a plurality of layers.

13. Sterilization process, using a sterile packing (1) according to claim 1, characterized in that the sterilization process the steps comprising:

filling said rigid part (6) of said container (2) with said at least one object (5) to be sterilized;

closing said inlet opening (11) and said discharge opening (13) by means of said non-rigid part (7);

sterilizing the container (2) by means of said sterilization fluid;

placing said sterilized container (2) in said at least one envelope (4);

creating a vacuum inside said envelope (4), and sealing said at least one envelope (4) around said container (2) while the vacuum inside said at least one envelope (4) is maintained.

* * * * *